US008798714B2

(12) United States Patent
Henning

(10) Patent No.: US 8,798,714 B2
(45) Date of Patent: Aug. 5, 2014

(54) MEDICAL APPARATUS INSTALLATION, AND METHOD FOR CONTROLLING A MEDICAL APPARATUS

(75) Inventor: Andre Henning, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/486,238

(22) Filed: Jun. 1, 2012

(65) Prior Publication Data

US 2012/0310079 A1 Dec. 6, 2012

(30) Foreign Application Priority Data

Jun. 1, 2011 (DE) .......................... 10 2011 076 880

(51) Int. Cl.
*A61B 5/05* (2006.01)

(52) U.S. Cl.
USPC ........... 600/411; 600/407; 600/410; 600/534; 600/527

(58) Field of Classification Search
USPC ........................................ 600/407, 409–411
See application file for complete search history.

(56) References Cited

U.S. PATENT DOCUMENTS

| | | | |
|---|---|---|---|
| 6,519,316 B1* | 2/2003 | Collins ............................ | 378/65 |
| 7,505,803 B2 | 3/2009 | Boese et al. | |
| 2003/0016851 A1* | 1/2003 | Kaufman et al. ............. | 382/131 |
| 2003/0036693 A1 | 2/2003 | Avinash et al. | |
| 2003/0195414 A1* | 10/2003 | Chang ............................ | 600/413 |
| 2004/0111045 A1 | 6/2004 | Sullivan et al. | |
| 2005/0190068 A1* | 9/2005 | Gentry et al. .................. | 340/665 |
| 2008/0204322 A1* | 8/2008 | Oswald et al. ................ | 342/465 |
| 2009/0178199 A1* | 7/2009 | Brauers et al. .................... | 5/611 |
| 2009/0306495 A1* | 12/2009 | Scarth et al. ................... | 600/415 |
| 2010/0191095 A1* | 7/2010 | Felblinger et al. ............ | 600/411 |
| 2010/0198053 A1* | 8/2010 | Miyazaki et al. ............. | 600/419 |

OTHER PUBLICATIONS

Lekkala et al., "EMFi—New Electret Material for Sensors and Actuators," 10th Int. Symposium on Electrets (1999), pp. 743-746.
Sakari et al., "An Electromechanical Film Sensor Based Wireless Ballistocardiographic Chair: Implementation and Performance," J Sign Process Syst, vol. 57 (2009), pp. 305-320.
Koivistoinen et al., "A New Method for Measuring the Ballistocardiogram using EMFi Sensors in a Normal Chair," Proceedings of the 26th Annual Int. Conf. of the IEEE EMBS (2004), pp. 2026-2029.

(Continued)

*Primary Examiner* — Tse Chen
*Assistant Examiner* — Joel F Brutus
(74) *Attorney, Agent, or Firm* — Schiff Hardin LLP

(57) ABSTRACT

In a medical apparatus and method, the apparatus installation has a placement device for a patient, into which placement device is integrated at least one electromechanical sensor. A signal evaluation device is supplied with the measurement signals generated with the at least one electromechanical sensor, for evaluation. The medical apparatus is connected with the signal evaluation device, and the medical apparatus acquires measurement signals that relate to breathing and/or cardiac activity of the patient with the at least one electromechanical sensor upon support of the patient on said placement device. Trigger signals are generated with the signal evaluation device based on the measurement signals which relate to breathing cycle and/or cardiac cycle of the patient. The operation of the medical apparatus is controlled based on the trigger signals.

13 Claims, 4 Drawing Sheets

(56) References Cited

OTHER PUBLICATIONS

Sakari et al., "An EMFi-film Sensor based Ballistocardiographic Chair: Performance and Cycle Extraction Method," IEEE Workshop on Signal Processing Systems Design and Implementation (2005), pp. 373-377.

Postolache et al., "New Approach on Cardiac Autonomic Control Estimation Based on BCG Processing," IEEE (2007), pp. 876-879.

Mendez et al., "Automatic Detection of sleep macrostructure based on bed sensors," 31st Annual Int. Conf. of the IEEE EMBS (2009), pp. 5555-5558.

Mendez et al., "Evaluation of the Sleep Quality based on bed sensor signals: Time-Variant Analysis," 32nd Annual Int. Conf. of the IEEE EMBS (2010), pp. 3994-3997.

Kortelainen et al., "Sleep Staging Based on Signals Acquired Through Bed Sensor," IEEE Transactions on Information Technology in Biomedicine, vol. 14, No. 3 (2010), pp. 776-785.

Postolache et al., "Physiological Parameters Measurement Based on Wheelchair Embedded Sensors and Advanced Signal Processing," IEEE Transactions on Instrumentation and Measurement, vol. 59, No. 10 (2010), pp. 2564-2574.

Jong-Myoung Kim et al., "Wireless Biomedical Signal Monitoring Device on Wheelchair using Noncontact Electro-mechanical Film Sensor," Proceedings of the 29th Annual Int. Conf. of the IEEE EMBS (2007), pp. 574-577.

\* cited by examiner

MEDICAL APPARATUS INSTALLATION, AND METHOD FOR CONTROLLING A MEDICAL APPARATUS

BACKGROUND OF THE INVENTION

1. Field of the Invention

The present invention concerns a method to control a medical apparatus, in particular for generation of images, which are optimally free of movement artifacts, of a tissue of the patient who moves due to cardiac activity and/or breathing, and/or for radiation therapy of a tissue of the patient who is moving due to cardiac activity and/or breathing. The invention also concerns an installation with such a medical apparatus and a computer to execute such a method, as well as a non-transitory data storage medium embodying programming instructions (commands) to execute such a method.

2. Description of the Prior Art

In the examination of tissue of a patient with an imaging apparatus, for example with an x-ray computed tomography apparatus, multiple 2D x-ray projections of the tissue are acquired respectively from different projection directions, most often during advancement of the tissue of the patient relative to the x-ray acquisition system of the x-ray computed tomograph. The goal of the examination is the generation of qualitatively high-grade and relevant images of the tissue based on the 2D x-ray projections, which images frequently form the basis for a medical diagnosis.

If tissue in the region of the torso of the patient is examined, the movement of such tissue that is caused by cardiac activity or breathing of the patient should also be taken into account in the generation of images of this tissue in order to be able to acquire high-quality images of the tissue that are free of movement artifacts.

For example, in the imaging of the heart itself as the tissue to be examined, in order to avoid such movement artifacts in the reconstructed slice images and 3D images of the heart, in the reconstruction of slice images and 3D images that takes place based on the acquired 2D x-ray projections of the heart, it is always sought to use only those 2D x-ray projections that have been acquired in the cardiac phase of the cardiac cycle of the patient in which the heart has performed practically no movement. It is typical to record an electrocardiogram (EKG) of the heart of the patient to determine the cardiac cycle of the heart of the patient.

For the generation of slice images and 3D images of the heart, 2D x-ray projections of the heart are normally acquired with parallel recording of the electrocardiogram over multiple cardiac cycles, and only thereafter is a selection made as to the 2D projections that are suitable for the reconstruction (based on the electrocardiogram). For this reason, this type of method is called a retrospective method.

In an alternative procedure, 2D x-ray projections of the heart are likewise acquired over multiple cardiac cycles, but based on an electrocardiogram acquired in parallel, acquisition of the respective projections takes place only when the heart is located in a cardiac phase at which it performs practically no movement. This procedure has the advantage that the patient is exposed to a lower dose of x-ray radiation.

If the patient has a low and uniform heart rate i.e., a uniform cardiac cycle, such as below 60 bpm (beats per minute), a relatively short time period around the 60% position of the RR interval can be identified by analysis of the RR interval in the EKG, in which time period 2D x-ray projections can be acquired in each cardiac cycle, for example. In this context, a "pulsing window" is established, which is a time window in which x-ray radiation is applied. Generally, it is preferable for the pulsing window to substantially coincide with the rest phase of the heart. Under such circumstances, a low dose of x-ray radiation for the acquisition of 2D x-ray projections from different projection directions that is required for the reconstruction of images of said heart is applied to the patient. A high image quality is simultaneously achieved.

The imaging procedure also can be implemented under consideration of breathing movements. A breathing belt is frequently used that embodies a motion sensor and is placed on the patient in the chest area to detect breathing movements. The detected breathing cycle is taken into account in the imaging.

SUMMARY OF THE INVENTION

An object of the invention is to provide an installation and a data storage medium of the aforementioned type that cause the operation of a medical apparatus to be controlled in an alternative manner.

According to the invention, this object is achieved by a method to control a medical apparatus of an installation having: a placement device for a patient, into which placement device is integrated at least one electromechanical sensor, and a signal evaluation device to which measurement signals generated by the at least one electromechanical sensor are supplied for evaluation. In the medical apparatus connected with the signal evaluation device, measurement signals which relate to the breathing and/or cardiac activity (physiological activity) of the patient are acquired with the at least one electromechanical sensor upon support of a patient on the placement device. Trigger signals are generated with the signal evaluation device based on the measurement signals that relate to the breathing cycle and/or the cardiac cycle of the patient; and the operation of the medical apparatus is controlled based on the trigger signals.

The invention proceeds from the consideration that the use of EKG electrodes is often laborious and uncomfortable for the patient. At least for male patients, the chest region must first be prepared by a partial removal of hair to apply the EKG electrodes. The use of an adhesive agent is most often required to arrange the EKG electrodes on the skin. Furthermore, given the use of EKG electrodes a certain dependency of the EKG signals with regard to the individual impedance of the skin of the patient occurs. Given the use of a breathing belt, this must also first be attached and fitted to a patient before an examination, which takes time.

The present invention foregoes the arrangement of measurement signal receivers (detectors) on the patient and instead at least one electromechanical sensor is arranged in a placement device on which the patient is borne. If the electromechanical sensor is arranged in the placement device such that it is located in the chest region of said patient when the patient is borne (supported) on the placement device, movements of the rib cage of the patient that are caused by cardiac and/or breathing activity can be registered with the electromechanical sensor as a result of the exertion of pressure on the electromechanical sensor, and corresponding measurement signals can be generated that characterize or identify the breathing and/or cardiac activity of the patient. The operation of a medical apparatus can be controlled or influenced with trigger signals derived from the measurement signals.

According to an embodiment of the invention, the placement device has a number of electromechanical sensors that are arranged in a two-dimensional matrix, the measurement signals of which are supplied to the signal evaluation device.

The use of multiple electromechanical sensors, and in particular their arrangement in an array or a two-dimensional matrix, simplifies the supportive positioning of the patient on the placement device since care does not need to be taken to insure that the chest region of the patient must be located over a specific electromechanical sensor. Furthermore, a number of measurement signals originating from different electromechanical sensors is provided in this embodiment, so that those measurement signals that appear to be or are best suited for the generation of trigger signals can be selected.

According to another embodiment of the invention, the signal evaluation device has a computer and a multiplexer, and the measurement signals originating from the electromechanical sensors are supplied by the multiplexer to the computer. The measurement signals are accordingly processed by time multiplexing, which allows measurement signals to be limited, or signals can be selected, to those that are relevant for the generation of trigger signals. These are normally the measurement signals with the largest amplitude values that originate from the electromechanical sensors that are arranged close to the heart of the patient, for example.

According to one embodiment of the invention, the measurement signals are evaluated by Fourier analysis and/or wavelet analysis in the signal evaluation device in order to generate trigger signals that relate to the breathing cycle and/or cardiac cycle of the patient. The measurement signals of each electromechanical sensor are advantageously subjected to Fourier analysis and/or wavelet analysis in order to identify the measurement signals, or the signal portions (components) of the measurement signals (including their signal energy) at a frequency that lies within the frequency bandwidth that is associated with a human heart (approximately 60 to 140 beats per minute), for example. The measurement signals that are to be associated with the breathing of the patient can be identified in the same manner.

According to a further embodiment of the invention, the position of the heart of the patient in relation to the placement device is determined, for example based on the signal strength or the signal amplitude of the relevant measurement signals, or based on the relevant signal portions of the measurement signals of the electromechanical sensors. Identification of the position of the heart of the patient in relation to the placement device is preferably based on a cross-correlation analysis of measurement signals, or signal portions of measurement signals, that respectively originate from electromechanical sensors that are adjacent to one another. The determination of the position of the heart enables those electromechanical sensors, or the measurement signals or signal portions originating from these electromechanical sensors (with which the cardiac activity can be detected or registered best) to be identified even more precisely. The goal is a qualitatively high-grade detection of the cardiac cycle of the patient (including the QRS complex) in order to be able to derive suitable trigger signals to control the medical apparatus.

The determination of the attitude of the heart in relation to the placement device additionally has the advantage that those electromechanical sensors can be better identified or localized whose measurement signals are best suited for determination of the breathing cycle of the patient. Those electromechanical sensors whose measurement signals pertain to the chest breathing and those electromechanical sensors whose measurement signals pertain to abdominal breathing can additionally be identified or localized. Variations in the breathing cycle can be determined and accounted for in this way depending on the region of the torso of the patient to generate suitable trigger signals.

In an embodiment of the invention, the medical apparatus is an imaging medical apparatus, and image information of the patient can be acquired with the imaging medical apparatus based on the trigger signals, in particular in the region of the breast or in the region of the abdomen of the patient.

According to a further embodiment of the invention, the medical apparatus is a radiation therapy apparatus, and the radiation treatment of a tissue of the patient is controlled based on the trigger signals.

The above object also is achieved according to the invention by an installation having a placement device for a patient, into which is integrated: at least one electromechanical sensor, a signal evaluation device to which the measurement signals generated with the at least one electromechanical sensor are supplied for evaluation, a medical apparatus that is connected with the signal evaluation device, and a computer operated by a computer program to execute any or all of the embodiments of the method described above.

In an embodiment of the inventive installation, the at least one electromechanical sensor (or, in the case of electromechanical sensors arranged in a two-dimensional matrix, the placement device) can be a piezoelectric sensor or piezoelectric sensors, or an EMFi (electromechanical film) sensor or EMFi sensors.

According to embodiments of the invention, the placement device can be a placement bearing plate of a placement bearing table, or a placement map which can be arranged on a patient bearing plate of a patient bearing table.

The medical apparatus can be a computed tomography apparatus, a C-arm x-ray apparatus, a PET apparatus, a SPECT apparatus, a magnetic resonance apparatus or a radiation therapy apparatus.

The above object also is achieved in accordance with the present invention by a non-transitory, computer-readable data storage medium encoded with programming instructions that, when the data storage medium is loaded into a control computer of a medical apparatus, cause the control computer to operate the medical apparatus in accordance with one or more of the above-described method embodiments.

DESCRIPTION OF THE PREFERRED EMBODIMENTS

Figure 1:
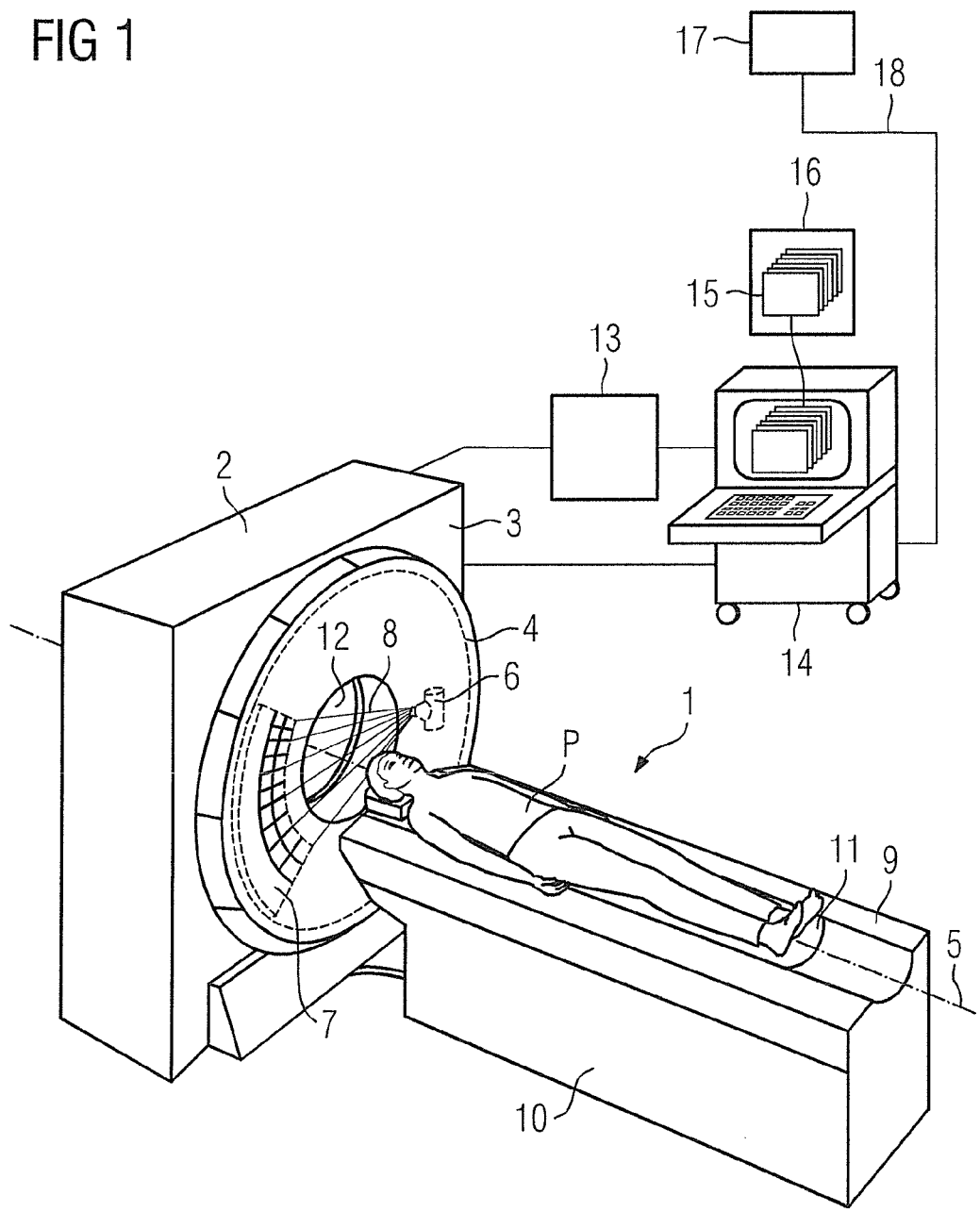
FIG. 1 schematically illustrates a medical apparatus in the form of a computed tomography apparatus.

Identical or functionally identical elements in the figures are provided throughout with the same reference characters. The representations in the figures are schematic and not necessarily true to scale. In the exemplary embodiments of the invention, the medical apparatuses are a computed tomography apparatus and a radiation therapy apparatus, which are discussed in the following and without limitation of the invention only insofar as is deemed necessary for comprehension of the invention.

The computed tomography apparatus 1 shown in FIG. 1 has a gantry 2 with a stationary part 3 and with a schematically indicated part 4 that can be rotated around a system axis 5. The part 4 is supported by means of a bearing (not shown in FIG. 1) such that it can rotate with respect to the stationary part 3. In the exemplary embodiment of the invention in FIG. 1, the rotatable part 4 has an x-ray system formed by an x-ray source 6 and an x-ray radiation detector 7 that are arranged opposite one another at the rotatable part 4. In the operation of the computed tomography apparatus 1, x-ray radiation 8 emanates from the x-ray source 6 in the direction of the x-ray radiation detector 7, penetrates a measurement subject, and is detected by the x-ray radiation detector 7 in the form of detector measurement data or detector measurement signals.

The computed tomography apparatus 1 furthermore has a patient bed 9 to support a patient P to be examined. The patient bed 9 has a bed base 10 on which is arranged a patient support plate 11 provided to actually support the patient P. The patient support plate 11 can be displaced in a motorized fashion in the direction of the system axis 5 relative to the bed base 10 such that it—together with the patient P—can be introduced into the opening 12 of the gantry 2 for the acquisition of 2D x-ray projections of the patient P, for example in a spiral scan.

The computational processing of the 2D x-ray projections acquired with the x-ray system and the reconstruction of slice images, 3D images or a 3D data set based on the detector measurement data or the detector measurement signals of the 2D x-ray projections takes place with an image computer 13 (schematically shown) of the computed tomography apparatus 1.

The computed tomography apparatus 1 also has a computer 14 with which computer programs are executed to operate and control the computed tomography apparatus 1. The computer 14 does not need to be designed as a separate computer 14, but can be integrated into the computed tomography apparatus 1.

In the exemplary embodiment of the invention, a computer program 15, which embodies code for executing the method according to the invention by controlling the computed tomography apparatus 1, is loaded into the computer 14. The computer program 15 represents a special operating mode (among others) for the computed tomography apparatus 1 and can have been loaded into the computer 14 from a portable non-transitory data storage medium (from a CD 16 or from a memory stick, for example) or from a server 17 via a network 18 (which can be a public network and also a network internal to the clinic or hospital).

Figure 2:
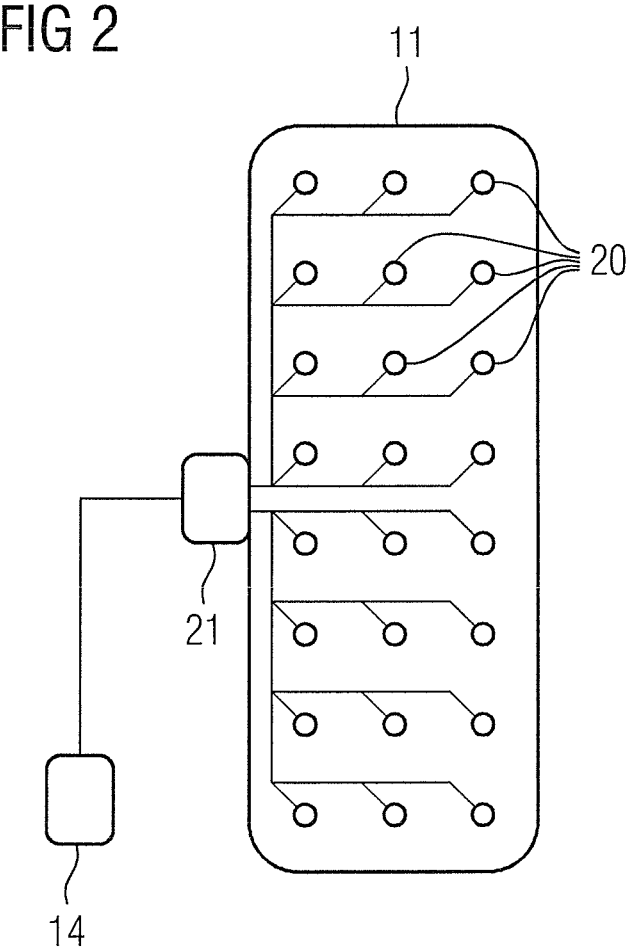
FIG. 2 shows a placement device in accordance with the invention with a number of integrated electromechanical sensors arranged in a two-dimensional matrix.

In the exemplary embodiment of the invention, a number of electromechanical sensors in the form of piezoelectric sensors 20 that are arranged in a two-dimensional matrix is integrated as a placement device for the patient P into the patient bearing plate 11. FIG. 2 shows in a schematic view the arrangement of the piezoelectric sensors 20 inside the patient support plate 11. The arrangement of the piezoelectric sensors 20 inside the patient support plate 11 is such that pressure can be and is exerted on the piezoelectric sensors 20 upon placement of the patient P on said patient support plate 11, such that these generate measurement signals. For the present invention it is primarily the dynamic pressure exertion on the piezoelectric sensors 20 due to the cardiac activity of the patient P as well as due to the rising and falling of the rib cage as a result of the breathing of the patient P that are relevant.

The piezoelectric sensors 20 are connected with a signal evaluation device that has a multiplexer 21 and a computer to evaluate the measurement signals. In the exemplary embodiment of the invention, the computer 14 forms the computer of the signal evaluation device. The measurement signals of the piezoelectric sensors 20 are supplied to the computer 14 via the multiplexer 21.

The computer 14 evaluates the measurement signals received from the multiplexer 21. In the exemplary embodiment of the invention it subjects the measurement signals of each piezoelectric sensor 20 to a Fourier and/or a wavelet analysis in order to initially identify those piezoelectric sensors 20 of the matrix whose measurement signals or whose signal portions of the measurement signals have a signal energy that is typical of cardiac activity and a frequency that lies within the frequency bandwidth that is associated with a human heart (approximately 60 to 140 beats per minute).

The position of the heart of the patient P in relation to the patient support plate 11 is determined via the piezoelectric sensors 20 that are identified in such a manner. In the exemplary embodiment of the invention, a cross-correlation analysis of the measurement signals which originate from identified adjacent electromechanical sensors 20 additionally takes place in order to determine the precise position of the heart of the patient P in relation to the patient support plate 11.

The activity of the heart of the patient is determined based on the analysis of the measurement signals of the identified piezoelectric sensors 20 arranged near the heart of the patient P. Ideally, the cardiac cycle of the patient P is determined so that trigger pulses to establish an aforementioned "pulsing windows" can be generated based on the determined cardiac cycle. For example, in this way the acquisition of x-ray projections of the chest region (in particular of the heart of the patient P) can be controlled, meaning that x-ray projections in which the heart of the patient P makes practically no movement are acquired only during the "pulsing window" established by the trigger pulses.

If the attitude of the heart in relation to the placement device is determined, those piezoelectric sensors 20 whose measurement signals are best suited to determine the breathing cycle of the patient P can be better identified or located. In particular, those piezoelectric sensors 20 whose measurement signals pertain to chest breathing and those mechanical sensors whose measurement signals pertain to diaphragmatic breathing can be identified or located.

The breathing cycle pertaining to chest breathing can inasmuch be determined based on the identified piezoelectric sensors 20 whose measurement signals pertain to the chest breathing. Ultimately, trigger signals with which at least one time period of the breathing cycle is established for acquisition of x-ray projections of the chest region of the patient P (in particular of the lungs of the patient) can be generated using the breathing cycle pertaining to chest breathing.

The breathing cycle pertaining to the diaphragmatic breathing can be determined in a comparable manner based on the identified piezoelectric sensors 20 whose measurement signals pertain to the diaphragmatic breathing. Ultimately, trigger signals with which at least one time period of the breathing cycle for acquisition of x-ray projections of the region of the abdomen of the patient P is established can be generated using the breathing cycle pertaining to the abdominal breathing.

With regard to the computed tomography apparatus 1, the respective determined or established trigger signals can be used for the prospective image generation method that was already described, in which x-ray projections are only acquired when optimally no movement of the torso of the patient P takes place, which movement is inherently caused by the cardiac and/or breathing activity. The trigger signals also can be used for a retrospective image generation method in which, after the acquisition of the x-ray projections based on the trigger signals, those x-ray projections that were acquired at a phase in which optimally no movement of the torso of the patient that was caused by the cardiac and/or breathing activity existed are selected for an image reconstruction.

The computed tomography apparatus 1 can thereby be used not only for imaging but also for planning of procedures (or also to plan a radiation therapy) in order to correlate the movement of a tissue of a patient that is to be therapeutically treated, for example with the breathing phases of said patient.

The imaging medical apparatus can moreover also be a C-arm x-ray apparatus, a PET apparatus, a SPECT apparatus or a magnetic resonance apparatus.

Figure 3:
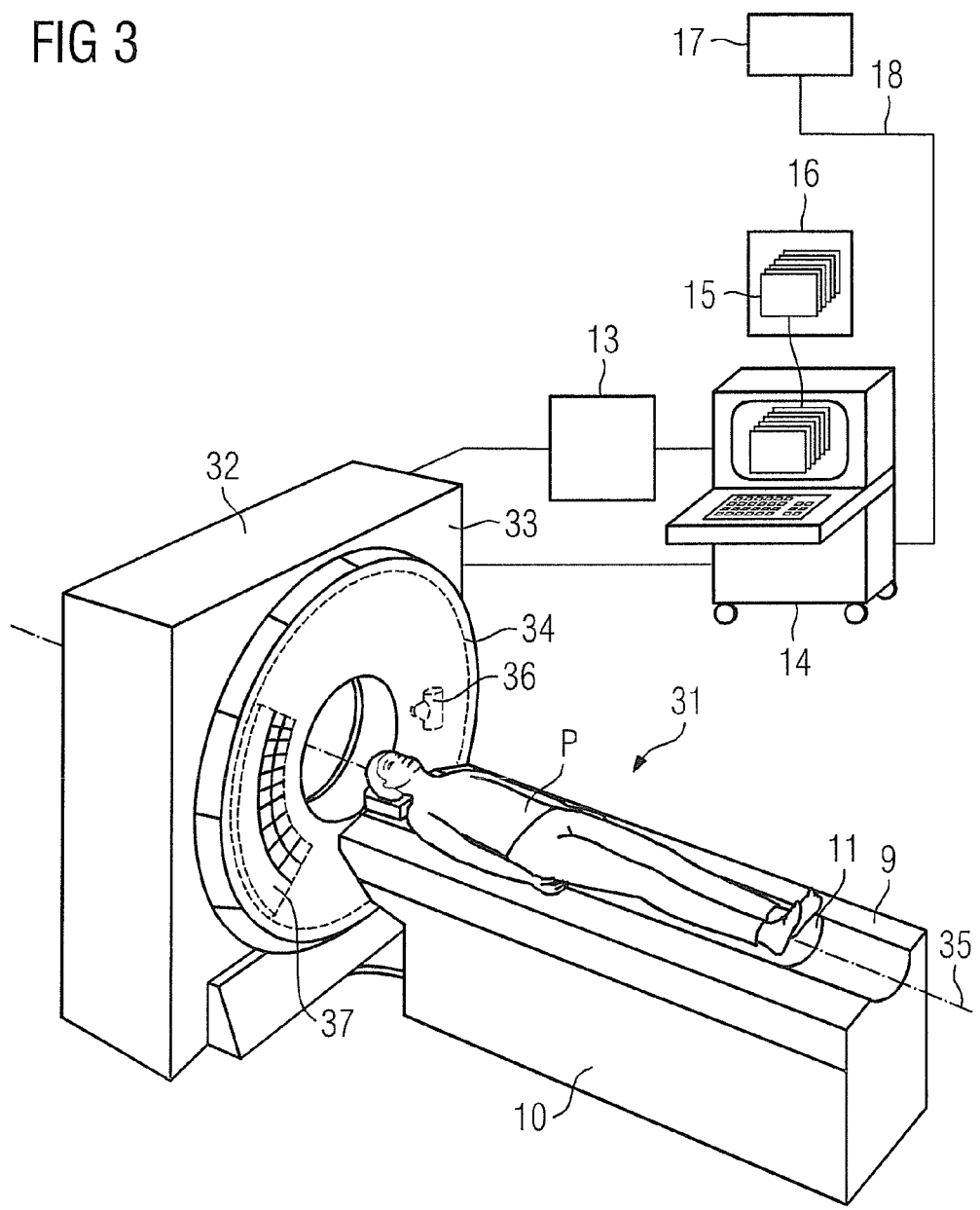
FIG. 3 schematically illustrates a medical apparatus in the form of a radiation therapy apparatus.

Moreover, the medical apparatus can also be a radiation therapy apparatus. FIG. 3 shows such a radiation therapy apparatus 31 in a schematic presentation, which apparatus 31 has a gantry 32 with a stationary part 33 and with a schematically indicated part 34 that is rotatable around a system axis 35, which part 34 is supported by means of a bearing (not shown in FIG. 3) such that it can rotate with respect to the stationary part 33. The rotatable part 34 has a therapeutic x-ray source 36 and an x-ray detector 37 arranged opposite this for MeV imaging. The remaining components of the radiation therapy apparatus 31 (such as the patient bed 9, etc.) essentially correspond to the components of the computer tomography apparatus 1, which is why these are provided with the same reference characters. The therapeutic x-ray source 36 serves to charge a tissue of the patient P that is to be treated therapeutically with therapeutic x-rays that have a photon energy in the MeV range.

In the radiation therapy apparatus 31, the trigger signals generated from the measurement signals of the piezoelectric sensors 20 of the patient bearing plate 11 are used to charge the tissue of the patient P with the therapeutic x-ray radiation only when optimally no movement (caused by the cardiac or breathing activity of the patient P) of the tissue to be therapeutically treated is present and/or when the tissue to be therapeutically treated is located in a defined therapy position, such that tissue that is not to be therapeutically treated is not also charged with x-ray radiation.

In contrast to the described exemplary embodiments of the invention, the piezoelectric sensors do not necessarily need to be integrated into the patient bearing plate. The possibility also exists to arrange the piezoelectric sensors in a placement mat that can be or, respectively, is placed on the patient bearing plate. This is particularly advantageous for already existing medical apparatuses that can simply be retrofitted in this manner.

Figure 4:
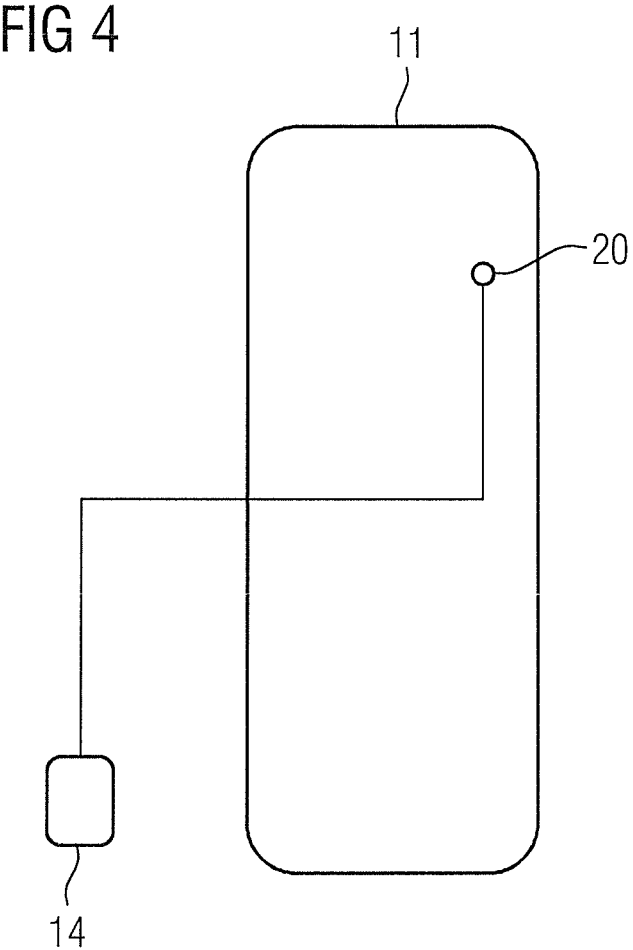
FIG. 4 shows a placement device in accordance with the invention with only one electromechanical sensor.

Also, a matrix of piezoelectric sensors does not necessarily need to exist. Insofar as it is appropriate, only one piezoelectric sensor can also be present in a patient bearing plate or placement mat. Using the patient bearing plate 11, FIG. 4 illustrates this simplified design in which only one piezoelectric sensor 20 is present. In this case, no multiplexer is required.

The electromechanical sensors do not necessarily need to be piezoelectric sensors. Rather, other electromechanical sensors can also be used with which "mechanical" effects on the sensors as a result of movements of a patient can be transduced into electrical signals.

The measurement signals of the electromechanical sensors can furthermore be used to determine the position of the patient on the placement device and the dimensions of the patient borne on said placement device.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to control a medical apparatus, comprising:
   placing a patient on a patient placement device of said medical apparatus that comprises a plurality of electromechanical sensors arranged in a two-dimensional array in said patient placement device;
   after placement of the patient on the patient placement device, operating said plurality electromechanical sensors to obtain respective measurement signals individually from the plurality electromechanical sensors, each of said plurality respective measurement signals representing breathing activity and cardiac activity of the patient;
   supplying the respective measurement signals from said plurality electromechanical sensors to a signal evaluation device and, in said signal evaluation device, automatically evaluating the respective measurement signals to identify a position of the heart of the patient with respect to the patient placement device;
   in said signal evaluation device, dependent on the position of the heart of the patient with respect to the patient placement device that has been identified, identifying respective electromagnetic sensors, among a plurality of electromagnetic sensors, that emit respective measurement signals representing chest breathing by the patient and identifying respective electromagnetic sensors, among said respective electromagnetic sensors, that emit respective measurement signals representing diaphragmatic breathing of the patient;
   at respectively different times, selectively operating said medical apparatus to interact with a chest region of the patient or to interact with an abdominal region of the patient;
   when operating said medical apparatus to interact with the chest region of the patient, generating a first trigger signal in said signal evaluation device exclusively from the respective measurement signals emitted by said electromagnetic sensors that represent chest breathing, and automatically triggering interaction of said medical apparatus with the chest region of the patient using said first trigger signal; and
   when operating said medical apparatus to interact with the abdominal region of the patient, generating a second trigger signal in said evaluation unit exclusively from the respective measurement signals emitted by the electromagnetic sensors that represent diaphragmatic breathing, and triggering interaction of said medical apparatus with the abdominal region of the patient dependent on said second trigger signal.

2. A method as claimed in claim 1 comprising supplying said respective measurement signals to said signal evaluation device by multiplexing said respective measurement signals.

3. A method as claimed in claim 1 comprising, in said signal evaluation device, evaluating said respective measurement signals to identify the position of the heart of the patient with respect to said patient placement device by implementing at least one analysis selected from the group consisting of Fourier analysis and a wavelet analysis.

4. A method as claimed in claim 1 comprising, in said signal evaluation device, identifying the position of the heart of the patient with respect to the patient placement device by implementing a cross-correlation analysis of respective measurement signals that respectively originate from electromechanical sensors that are adjacent to each other in an array.

5. A method as claimed in claim 1 wherein said medical apparatus is a medical imaging apparatus and comprising acquiring image information from the patient on said patient placement device at a time triggered by said trigger signals.

6. A method as claimed in claim 1 wherein said medical apparatus is a radiation therapy apparatus configured to implement radiation treatment of tissue of the patient on said patient placement device, and comprising triggering emission of radiation in said radiation treatment dependent on said trigger signals.

7. A medical apparatus comprising
a medical device configured to interact with a patient;
a patient placement device in said medical apparatus adapted to receive the patient thereon, said patient placement device comprising a plurality of electromechanical sensors arranged in a two-dimensional array in said patient placement device;
an evaluation unit configured to operate said plurality electromechanical sensors to obtain respective measurement signals individually from the plurality electromechanical sensors, each of said plurality respective measurement signals representing breathing activity and cardiac activity of the patient;
a control unit receiving the respective measurement signals from said plurality electromechanical sensors being configured to automatically evaluate the respective measurement signals to identify a position of the heart of the patient with respect to the patient placement device;
said evaluation unit being configured to identify, dependent on the position of the heart of the patient with respect to the patient placement device that has been identified, respective electromagnetic sensors, among a plurality of electromagnetic sensors, that emit respective measurement signals representing chest breathing by the patient and to identify respective electromagnetic sensors, among said respective electromagnetic sensors, that emit respective measurement signals representing diaphragmatic breathing of the patient;
a control unit configured to operate said medical apparatus at respectively different times to selectively interact with a chest region of the patient or to interact with an abdominal region of the patient;
when said control unit operates said medical apparatus to interact with the chest region of the patient, said evaluation unit being configured to generate a first trigger signal exclusively from the respective measurement signals emitted by said respective electromagnetic sensors that represent chest breathing, and to supply said first trigger signal to the control unit to automatically trigger interaction of said medical apparatus with the chest region of the patient using said first trigger signal; and
when said control unit operates said medical apparatus to interact with the abdominal region of the patient, said signal evaluation unit being configured to generate a second trigger signal exclusively from the respective measurement signals emitted by the respective electromagnetic sensors that represent diaphragmatic breathing, and to supply said second trigger signal to said control unit to trigger interaction of said medical apparatus with the abdominal region of the patient dependent on said second trigger signal.

8. A medical apparatus as claimed in claim 7 wherein at least one electromechanical sensor is a sensor selected from the group consisting of piezoelectric sensors and electromechanical film sensors.

9. A medical apparatus as claimed in claim 7 wherein said patient placement device is a patient support plate of a patient's support table.

10. A medical apparatus as claimed in claim 7 wherein said patient placement device is a placement mat configured to be arranged on a patient support plate of a patient support table.

11. A medical apparatus as claimed in claim 7 comprising a multiplexer that supplies respective measurement signals from the plurality of electromechanical sensors to said processor by multiplexing.

12. A medical apparatus as claimed in claim 7 wherein said medical apparatus is an apparatus selected from the group consisting of a computed tomography apparatus, a C-arm x-ray apparatus, a PET apparatus, a SPECT apparatus, a magnetic resonance apparatus, and a radiation therapy apparatus.

13. A non-transitory, computer-readable data storage medium encoded with programming instructions, said data storage medium being loaded into a computerized control and evaluation system of a medical apparatus that also comprises a medical device that interacts with a patient, and a patient placement device adapted to receive the patient thereon and having a plurality of electromagnetic sensors arranged in a two-dimensional array therein, said programming instructions causing said computerized control and evaluation system to:
after placement of the patient on the patient placement device, operate electromechanical sensors to obtain respective measurement signals individually from the plurality of electromechanical sensors, each of said respective measurement signals representing breathing activity and cardiac activity of the patient;
automatically evaluate the respective measurement signals to identify a position of the heart of the patient with respect to the patient placement device;
dependent on the position of the heart of the patient with respect to the patient placement device that has been identified, identify respective electromagnetic sensors, among said plurality of electromagnetic sensors, that emit respective measurement signals representing chest breathing by the patient and identify respective electromagnetic sensors, among a plurality of electromagnetic sensors, that emit respective measurement signals representing diaphragmatic breathing of the patient;
at respectively different times, selectively operate said medical apparatus to interact with a chest region of the patient or to interact with an abdominal region of the patient;
when operating said medical apparatus to interact with the chest region of the patient, generate a first trigger signal exclusively from the respective measurement signals emitted by said electromagnetic sensors that represent chest breathing, and automatically trigger interaction of said medical apparatus with the chest region of the patient using said first trigger signal; and
when operating said medical apparatus to interact with the abdominal region of the patient, generate a second trigger signal exclusively from the respective measurement signals emitted by the electromagnetic sensors that represent diaphragmatic breathing, and trigger interaction of said medical apparatus with the abdominal region of the patient dependent on said second trigger signal.

* * * * *